US012588891B2

(12) United States Patent
Imai

(10) Patent No.: US 12,588,891 B2
(45) Date of Patent: Mar. 31, 2026

(54) ACOUSTIC WAVE DIAGNOSTIC APPARATUS AND METHOD OF CONTROLLING ACOUSTIC WAVE DIAGNOSTIC APPARATUS

(71) Applicant: FUJIFILM Corporation, Tokyo (JP)

(72) Inventor: Yoshiro Imai, Kanagawa (JP)

(73) Assignee: FUJIFILM Corporation, Tokyo (JP)

( * ) Notice: Subject to any disclaimer, the term of this patent is extended or adjusted under 35 U.S.C. 154(b) by 170 days.

(21) Appl. No.: 17/105,785

(22) Filed: Nov. 27, 2020

(65) Prior Publication Data

US 2021/0077066 A1    Mar. 18, 2021

Related U.S. Application Data

(63) Continuation of application No. PCT/JP2019/020204, filed on May 22, 2019.

(30) Foreign Application Priority Data

Jul. 2, 2018    (JP) ................................. 2018-125942

(51) Int. Cl.
    *A61B 8/14*        (2006.01)
    *A61B 8/00*        (2006.01)
(52) U.S. Cl.
    CPC .............. *A61B 8/14* (2013.01); *A61B 8/4272* (2013.01); *A61B 8/4444* (2013.01); *A61B 8/461* (2013.01)
(58) Field of Classification Search
    CPC ....... A61B 8/14; A61B 8/4272; A61B 8/4444; A61B 8/461; A61B 5/0035; A61B 8/08;
    (Continued)

(56) References Cited

U.S. PATENT DOCUMENTS 10,140,421 B1 * 11/2018 Bernard ................. G06N 3/084
2008/0267499 A1    10/2008 Deischinger et al.
(Continued)

FOREIGN PATENT DOCUMENTS

JP        2009-165615 A    7/2009
JP        2013-111434 A    6/2013
          (Continued)

OTHER PUBLICATIONS

The extended European search report issued by the European Patent Office on Jul. 28, 2021, which corresponds to European Patent Application No. 19830093.1-1126 and is related to U.S. Appl. No. 17/105,785.

(Continued)

*Primary Examiner* — Rochelle D Turchen
(74) *Attorney, Agent, or Firm* — Studebaker Brackett PLLC

(57)        ABSTRACT

An ultrasound diagnostic apparatus 1 sequentially displays ultrasound images of a plurality of continuous frames during imaging on a display unit 8, and includes a measurement target recognition unit 9 that automatically recognizes a measurement target included in an ultrasound image of a present frame displayed on the display unit 8, a measurement algorithm setting unit 12 that sets a measurement algorithm for the measurement target recognized by the measurement target recognition unit 9, and a measurement unit 10 that measures the measurement target based on the measurement algorithm set by the measurement algorithm setting unit 12 and displays a measurement result on the display unit 8 to be superimposed on the ultrasound image of the present frame.

15 Claims, 8 Drawing Sheets

(58) Field of Classification Search
CPC ..... A61B 5/0095; A61B 5/7425; A61B 8/463;
A61B 8/465; A61B 8/467; A61B 8/468;
A61B 8/5223; A61B 8/469
See application file for complete search history.

(56) References Cited

U.S. PATENT DOCUMENTS

| | | | |
|---|---|---|---|
| 2009/0180677 A1 | 7/2009 | Li et al. | |
| 2009/0198132 A1* | 8/2009 | Pelissier | ............. G01S 7/52084 |
| | | | 600/443 |
| 2010/0322495 A1* | 12/2010 | Collet-Billon | ....... A61B 8/0875 |
| | | | 382/131 |
| 2011/0170755 A1 | 7/2011 | Buelow et al. | |
| 2013/0190600 A1 | 7/2013 | Gupta et al. | |
| 2014/0100442 A1 | 4/2014 | Begin et al. | |
| 2016/0074006 A1 | 3/2016 | Patruno et al. | |
| 2017/0124700 A1 | 5/2017 | Sarojam et al. | |
| 2017/0360402 A1 | 12/2017 | de Jonge et al. | |
| 2017/0360412 A1* | 12/2017 | Rothberg | ............. A61B 8/5223 |
| 2018/0161010 A1 | 6/2018 | Choi et al. | |
| 2018/0330518 A1* | 11/2018 | Choi | ........................ A61B 8/14 |

FOREIGN PATENT DOCUMENTS

| | | |
|---|---|---|
| JP | 2015-100479 A | 6/2015 |
| JP | 2017-109074 A | 6/2017 |
| WO | 2016194161 A1 | 12/2016 |
| WO | WO-2018140415 A1 * | 8/2018 ......... A61B 1/00011 |

OTHER PUBLICATIONS

International Search Report issued in PCT/JP2019/020204; mailed Aug. 6, 2019.
International Preliminary Report on Patentability and Written Opinion issued in PCT/JP2019/020204; issued Jan. 5, 2021.
An Office Action mailed by the China National Intellectual Property Administration on Oct. 27, 2023, which corresponds to Chinese Patent Application No. 201980044151.8 and is related to U.S. Appl. No. 17/105,785; with English translation.
An Office Action mailed by China National Intellectual Property Administration on May 8, 2024, which corresponds to Chinese Patent Application No. 201980044151.8 and is related to U.S. Appl. No. 17/105,785; with English language translation.
Extended European Search Report issued in EP 24186316.6-1122 by the European Patent Office on Sep. 25, 2024, which is related to U.S. Appl. No. 17/105,785.
An Office Action; mailed by the China National Intellectual Property Administration of the People's Republic of China on Aug. 15, 2024, which corresponds to Chinese Patent Application No. 201980044151.8 and is related to U.S. Appl. No. 17/105,785; with English language translation.

* cited by examiner

FIG. 6

GALLBLADDER: MAJOR AXIS 5.6 cm
MINOR AXIS 3.1 cm

OPTIMUM IMAGE
IS SAVED

PR, PA, C2A, ML2, A1, 8

U1, C1A, ML1, C2B, C1B

GALLBLADDER: CURRENT VALUE X cm
MAXIMUM VALUE Y cm

PR, A1, 8

U1, C1A, ML1, C1B

ACOUSTIC WAVE DIAGNOSTIC APPARATUS AND METHOD OF CONTROLLING ACOUSTIC WAVE DIAGNOSTIC APPARATUS

CROSS-REFERENCE TO RELATED APPLICATIONS

This application is a Continuation of PCT International Application No. PCT/JP2019/020204 filed on May 22, 2019, which claims priority under 35 § 119(a) to Japanese Patent Application No, 2018-125942 filed on Jul. 2, 2018, The above application is hereby expressly incorporated by reference, in its entirety, into the present application.

BACKGROUND OF THE INVENTION

1. Field of the Invention

The present invention relates to an acoustic wave diagnostic apparatus and a method of controlling an acoustic wave diagnostic apparatus, and in particular, to an acoustic wave diagnostic apparatus and a method of controlling an acoustic wave diagnostic apparatus that measure a part on an acoustic wave image.

2. Description of the Related Art

In recent years, a medical acoustic wave diagnostic apparatus generally has a measurement function of measuring a length, a size, an area, and the like of various organs, lesions, and the like included in an acquired acoustic wave image. In order to measure a measurement target, normally, a user operates a caliper, that is, a cursor using an input device that inputs coordinates, such as a touch pad, a trackball, or a mouse, and sets a measurement point, a region of interest, or the like on a display image. In this case, in a case where a manual operation of the user is performed, an experience, proficiency, or the like of the user affects, various attempts have been made to automate the operation.

For example, JP2013-111434A discloses an ultrasound diagnostic apparatus that, in a case where a position of a caliper for use in measuring a measurement target is input from a user through an operating unit on one acquired ultrasound image, corrects the position of the caliper to an appropriate position by executing image processing on a peripheral region of the input caliper. In the ultrasound diagnostic apparatus disclosed in JP2013-111434A, for example, in a case where a pair of calipers for measuring a distance between two points on the ultrasound image is input by the user, a pair of calipers is corrected to appropriate positions, and a length of the measurement target is measured based on a pair of corrected calipers.

SUMMARY OF THE INVENTION

However, in the ultrasound diagnostic apparatus disclosed in JP2013-111434A, since one ultrasound image representing an optimum cross section for measurement needs to be acquired, and the user needs to manually dispose a caliper on one acquired ultrasound image, there is a problem in that the user is required to spend a lot of labor and time in executing measurement.

Furthermore, in acquiring an optimum ultrasound image for measurement, the user needs to determine the optimum cross section for measurement by viewing ultrasound images that are sequentially displayed on a display unit.

Thus, when an inexperienced user executes measurement, it is difficult for the user to acquire the ultrasound image representing the optimum cross section for measurement.

The invention has been accomplished in order to solve such a problem in the related art, and an object of the invention is to provide an acoustic wave diagnostic apparatus and a method of controlling an acoustic wave diagnostic apparatus capable of conveniently and exactly executing measurement.

In order to achieve the above-described object, the invention provides an acoustic wave diagnostic apparatus that sequentially displays acoustic wave images of a plurality of continuous frames during imaging on a display unit. The acoustic wave diagnostic apparatus comprises a measurement target recognition unit that automatically recognizes a measurement target included in an acoustic wave image of a present frame displayed on the display unit, a measurement algorithm setting unit that sets a measurement algorithm for the measurement target recognized by the measurement target recognition unit, and a measurement unit that measures the measurement target based on the measurement algorithm set by the measurement algorithm setting unit and displays a measurement result on the display unit to be superimposed on the acoustic wave image of the present frame.

It is preferable that the acoustic wave diagnostic apparatus further comprises an image memory, an optimum image determination unit that determines whether or not the acoustic wave image of the present frame among the plurality of continuous frames during imaging includes an optimum cross section of the measurement target, and a saving controller that, in a case where the optimum image determination unit determines that the acoustic wave image of the present frame includes the optimum cross section of the measurement target, saves the acoustic wave image of the present frame and the measurement result in the image memory.

The acoustic wave diagnostic apparatus may further comprise an operating unit through which the user performs an input operation, and the saving controller may display the acoustic wave image saved in the image memory by the saving controller on the display unit based on a user's operation through the operating unit.

In this case, the saving controller may overwrite and save the acoustic wave image of the present frame and the measurement result in the image memory in a case where the optimum image determination unit determines that the acoustic wave image of the present frame includes the optimum cross section of the measurement target.

Alternatively, the saving controller may add and save the acoustic wave image of the present frame and the measurement result in the image memory in a case where the optimum image determination unit determines that the acoustic wave image of the present frame includes the optimum cross section of the measurement target.

The acoustic wave diagnostic apparatus may further comprise a notification unit that gives notification to the user in a case where the acoustic wave image of the present frame and the measurement result are saved by the saving controller.

The measurement result may include a measurement value, and the optimum image determination unit may determine that the acoustic wave image of the present frame includes the optimum cross section of the measurement target in a case where the measurement value is a maximum in the acoustic wave image of the present frame among the plurality of continuous frames during imaging.

The measurement target recognition unit may calculate likelihood representing measurement target likeness of the measurement target to be recognized, and the optimum image determination unit may determine that the acoustic wave image of the present frame includes the optimum cross section of the measurement target in a case where the likelihood is a maximum in the acoustic wave image of the present frame among the plurality of continuous frames during imaging.

The saving controller may save the acoustic wave images of all frames captured in the past a determined time from the present frame among the plurality of continuous frames during imaging and the measurement results in the image memory.

In this case, the saving controller may save the acoustic wave image of a frame determined to include the optimum cross section of the measurement target by the optimum image determination unit among the plurality of continuous frames during imaging while providing a flag and may save the acoustic wave image in the image memory and may select and display the acoustic wave image provided with the flag among the plurality of acoustic wave images saved in the image memory on the display unit based on a user's operation through the operating unit.

In a case where a plurality of the measurement targets are recognized in the acoustic wave image of the present frame by the measurement target recognition unit, the measurement algorithm setting unit may set the measurement algorithm for each of the plurality of measurement targets in the acoustic wave image of the present frame, and the measurement unit may measure the plurality of measurement targets based on the measurement algorithms corresponding to the plurality of measurement targets in the acoustic wave image of the present frame and may display a plurality of the measurement results on the display unit to be superimposed on the acoustic wave image of the present frame.

The acoustic wave diagnostic apparatus may further comprise a measurement control switch that is operated by the user to perform a command to start and a command to end a series of measurement operation including the recognition of the measurement target by the measurement target recognition unit, the setting of the measurement algorithm by the measurement algorithm setting unit, and the measurement of the measurement target by the measurement unit.

In this case, it is preferable that the acoustic wave diagnostic apparatus further comprises an acoustic wave probe that transmits and receives acoustic waves to and from a subject, and the measurement control switch is disposed in the acoustic wave probe.

The invention provides a method of controlling an acoustic wave diagnostic apparatus that sequentially displays acoustic wave images of a plurality of continuous frames during imaging on a display unit. The method comprises automatically recognizing a measurement target included in an acoustic wave image of a present frame displayed on the display unit, setting a measurement algorithm for the recognized measurement target, measuring the measurement target based on the set measurement algorithm, and displaying a measurement result on the display unit to be superimposed on the acoustic wave image of the present frame.

According to the invention, the acoustic wave diagnostic apparatus that sequentially displays the acoustic wave images of a plurality of continuous frames during imaging on the display unit comprises the measurement target recognition unit that automatically recognizes the measurement target included in the acoustic wave image of the present frame displayed on the display unit, a measurement algorithm setting unit that sets the measurement algorithm for the measurement target recognized by the measurement target recognition unit, and the measurement unit that measures the measurement target based on the measurement algorithm set by the measurement algorithm setting unit and displays the measurement result on the display unit to be superimposed on the acoustic wave image of the present frame, Thus, it is possible to conveniently and exactly execute measurement.

BRIEF DESCRIPTION OF THE DRAWINGS

FIG. 6 is a block diagram showing the configuration of an ultrasound diagnostic apparatus according to Embodiment 2 of the invention.

DESCRIPTION OF THE PREFERRED
EMBODIMENTS

Hereinafter, embodiments of the invention will be described referring to the accompanying drawings.

Embodiment 1

Figure 1:
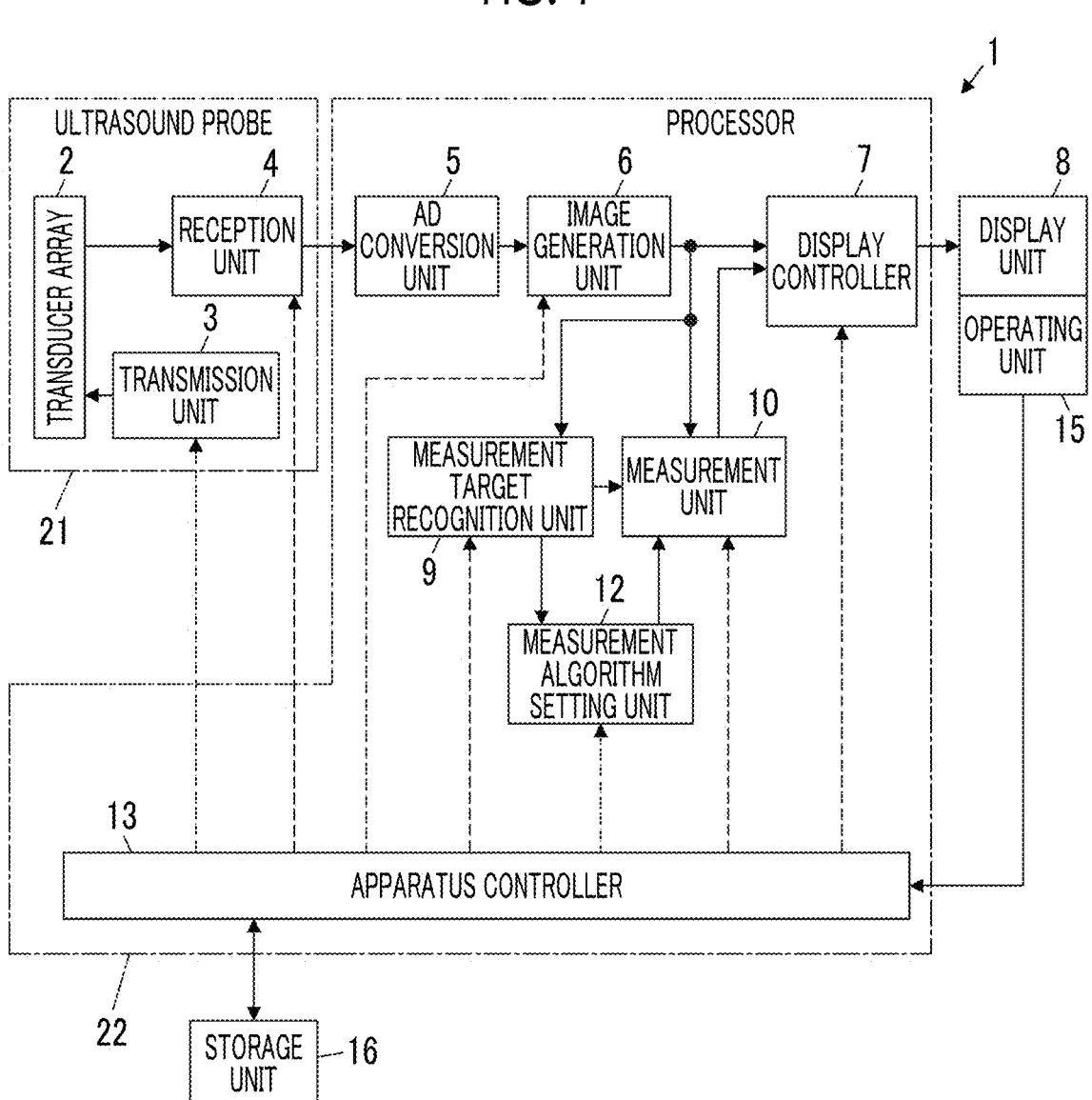
FIG. 1 is a block diagram showing the configuration of an ultrasound diagnostic apparatus according to Embodiment 1 of the invention.

FIG. 1 shows the configuration of an ultrasound diagnostic apparatus 1 according to Embodiment 1 of the invention. As shown in FIG. 1, the ultrasound diagnostic apparatus 1 comprises a transducer array 2, and a transmission unit 3 and a reception unit 4 are connected to the transducer array 2. An analog-to-digital (AD) conversion unit 5, an image generation unit 6, a display controller 7, and a display unit 8 are connected sequentially to the reception unit 4, and an operating unit 15 is disposed to be superimposed on the display unit 8. A measurement target recognition unit 9 and a measurement unit 10 are connected to the image generation unit 6, the measurement unit 10 is connected to the measurement target recognition unit 9, and the display controller 7 is connected to the measurement unit 10. A measurement algorithm setting unit 12 is connected to the measurement target recognition unit 9, and the measurement unit 10 is connected to the measurement algorithm setting unit 12.

An apparatus controller 13 is connected to the transmission unit 3, the reception unit 4, the image generation unit 6, the display controller 7, the measurement target recognition unit 9, the measurement unit 10, and the measurement algorithm setting unit 12, and the operating unit 15 and a storage unit 16 are connected to the apparatus controller 13.

The transducer array 2, the transmission unit 3, and the reception unit. 4 configure an ultrasound probe 21, and the AD conversion unit 5, the image generation unit 6, the display controller 7, the measurement target recognition unit 9, the measurement unit 10, the measurement algorithm setting unit 12, and the apparatus controller 13 configure a processor 22.

The transducer array 2 of the ultrasound probe 21 shown in FIG. 1 has a plurality of ultrasound transducers arranged in a one-dimensional or two-dimensional manner. The ultrasound transducers transmit ultrasonic waves in compliance with drive signals supplied from the transmission unit 3, receive reflected waves from a subject, and output reception signals, Each ultrasound transducer is constituted by forming electrodes at both ends of a piezoelectric body made of, for example, piezoelectric ceramic represented by lead zirconate titanate (PZT), a polymer piezoelectric element represented by poly vinylidene di fluoride (PVDF), piezoelectric single crystal represented by lead magnesium niobate-lead titanate (PMN-PT), or the like.

The transmission unit 3 of the ultrasound probe 21 includes, for example, a plurality of pulse generators, and adjusts a delay amount of each drive signal based on a transmission delay pattern selected according to a control signal from the apparatus controller 13 such that the ultrasonic waves transmitted from a plurality of ultrasound transducers of the transducer array 2 form an ultrasonic beam, and supplies the drive signals to a plurality of ultrasound transducers. In this way, in a case where a pulsed or continuous-wave voltage is applied to the electrodes of each of the ultrasound transducers of the transducer array 2, the piezoelectric body expands and contracts to generate a pulsed or continuous-wave ultrasonic wave from each of the ultrasound transducers, An ultrasonic beam is formed from a combined wave of the ultrasonic waves.

The transmitted ultrasonic beam is reflected by, for example, a target, such as a part of the subject, and propagates toward the transducer array 2 of the ultrasound probe 21. The ultrasonic waves that propagate toward the transducer array 2 in this way are received by the respective ultrasound transducers configuring the transducer array 2. In this case, each of the ultrasound transducers configuring the transducer array 2 expands and contracts with reception of a propagating ultrasound echo to generate an electrical signal, and outputs the electrical signal to the reception unit 4 as a reception signal. Though not shown, the reception unit 4 has an amplification unit that amplifies the reception signal input from each of the ultrasound transducers, and a signal amplified by the amplification unit is sent to the AD conversion unit 5.

The AD conversion unit 5 of the processor 22 converts the reception signal sent from the reception unit 4 into digitized element data, and sends the element data to the image generation unit 6.

Figure 2:
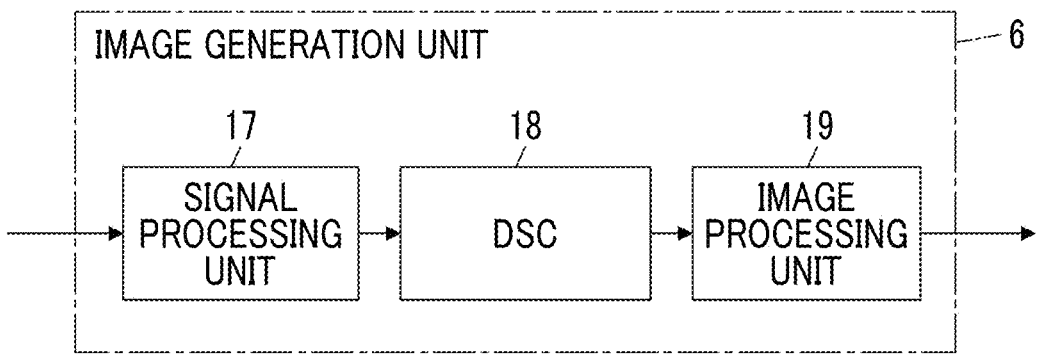
FIG. 2 is a block diagram showing the internal configuration of an image generation unit in Embodiment 1 of the invention.

As shown in FIG. 2, the image generation unit 6 of the processor 22 has a configuration in which a signal processing unit 17, a digital scan converter (DSC) 18, and an image processing unit 19 are connected in series. The signal processing unit 17 executes reception focus processing of giving a delay to each piece of element data compliant with a set sound speed based on a reception delay pattern selected according to a control signal from the apparatus controller 13 and performing addition (phasing addition). With the reception focus processing, a sound ray signal in which a focus of the ultrasound echo is narrowed is generated. The signal processing unit 17 performs correction of attenuation of the generated sound ray signal due to a propagation distance according to a depth of a reflection position of the ultrasonic wave, and then, executes envelope detection processing to generate a B mode image signal as tomographic image information regarding a tissue in the subject. The B mode image signal generated in this way is output to the DSC 18.

The DSC 18 raster-converts the B mode image signal into an image signal compliant with a normal television signal scanning system, that is, a B mode image. The image processing unit 19 executes various kinds of necessary image processing, such as brightness correction, gradation correction, sharpness correction, and color correction, on image data obtained in the DSC 18, and then, outputs the B mode image signal to the display controller 7, the measurement target recognition unit 9, and the measurement unit 10. Hereinafter, the 13 mode image is simply referred to as an ultrasound image.

The measurement target recognition unit 9 of the processor 22 recognizes a measurement target included in the ultrasound image by performing image recognition on the ultrasound image generated by the image generation unit 6. Here, the measurement target can include a part to be a target of measurement, such as an organ, or a lesion part, such as a tumor, a cyst, or bleeding. For example, the measurement target recognition unit 9 can distinguish the measurement target in the ultrasound image using machine learning, such as deep learning. In this case, for example, a neural network can be constructed by making the measurement target recognition unit 9 learn a large amount of typical pattern data for the measurement target as positive data in advance and learn a large amount of pattern data other than the typical pattern data for the measurement target as negative data in advance. The measurement target recognition unit 9 can distinguish a measurement target by calculating a length or the like of a characteristic portion for patterns included in the ultrasound image and classifying the patterns into learned pattern data using a calculation result and the constructed neural network.

In this case, the measurement target recognition unit 9 can recognize the measurement target by providing likelihood for the learned pattern data to the patterns included in the ultrasound image and performing threshold value determination for the likelihood. Here, the likelihood is a value representing likelihood of a pattern included in the ultrasound image for a plurality of pieces of learned pattern data. For example, in a case of the likelihood of the pattern included in the ultrasound image is high with respect to pattern data of a gallbladder, there is a high probability that the pattern included in the ultrasound image is the gallbladder.

Here, as a method of machine learning, for example, a method described in Csurka et al.: Visual Categorization with Bags of Keypoints, Proc. of ECCV Workshop on Statistical Learning in Computer Vision, pp. 59-74 (2004) or the like can be used.

For example, the measurement target recognition unit 9 may distinguish a measurement target by storing typical pattern data as a template in advance, calculating similarity to pattern data while searching an image with a template, and considering that a measurement target is present at a place where similarity is equal to or greater than a threshold value and is a maximum.

The measurement algorithm setting unit 12 of the processor 22 sets a measurement algorithm for the measurement target recognized by the measurement target recognition unit 9. The measurement algorithm setting unit 12 stores measurement algorithms corresponding to a plurality of parts or the like to be a measurement target as an association table in advance, and sets a measurement algorithm with reference to the association table in a case where the measurement target is determined.

Here, in general, there are different measurement rules for the measurement targets. The measurement rule is a rule regarding which portion is measured and how the portion is measured with respect to a specific measurement target. For example, in a case where the measurement target is a gallbladder, the measurement rule is that a line segment, which as two points on an inner wall of a gallbladder region included in the ultrasound image as end points, passes through the center of gravity of the gallbladder region, and has a maximum distance, is decided as a measurement line, and a length of the decided line segment is measured. Furthermore, for example, in a case where the measurement target is a kidney, the measurement rule determines that a length between two points having a maximum distance among two points on a boundary of a kidney region included in the ultrasound image is measured. The measurement algorithm defines calculation means for executing such a measurement rule, and is different for each measurement target.

Here, the algorithm defines calculation means for achieving the purpose, such as measurement. For example, the algorithm is implemented in the apparatus as a software program and is executed by a central processing unit (CPU). As the measurement algorithm set in the measurement algorithm setting unit 12, a known algorithm that is generally used can be used.

The measurement unit 10 of the processor 22 measures the measurement target recognized by the measurement target recognition unit 9 based on the measurement algorithm set by the measurement algorithm setting unit 12 and displays a measurement result on the display unit 8 through the display controller 7, Here, the measurement result that is displayed on the display unit 8 by the measurement unit 10 may include a name of the measurement target, a measurement line and a caliper used for measurement, and the like in addition to a measurement value of the measurement target.

The display controller 7 of the processor 22 executes predetermined processing on the ultrasound image generated by the image generation unit 6 and displays the ultrasound image on the display unit 8 under the control of the apparatus controller 13. The display controller 7 displays the measurement result and the like calculated by the measurement unit 10 on the display unit 8.

The display unit 8 of the ultrasound diagnostic apparatus 1 has a display screen (not shown), and displays the ultrasound image generated by the image generation unit 6, the measurement result calculated by the measurement unit 10, and the like on the display screen under the control of the display controller 7. The display unit 8 includes, for example, a display device, such as a liquid crystal display (LCD) or an organic electroluminescence display (organic EL display).

The operating unit 15 of the ultrasound diagnostic apparatus 1 is provided for a user to perform an input operation, and includes a touch sensor disposed to be superimposed on the display unit 8. The touch sensor is disposed to be superimposed on the display screen of the display unit 8, and is provided for the user to perform an input operation through a touch operation to bring a finger of the user, a stylus pen, or the like into contact with or close to the display screen. Information input by the user through the touch sensor of the operating unit 15 is sent to the apparatus controller 13.

The storage unit 16 of the ultrasound diagnostic apparatus 1 stores an operation program and the like of the ultrasound diagnostic apparatus 1, and a recording medium, such as a hard disc drive (HDD), a solid state drive (SSD), a flexible disc (FD), a magneto-optical disc (MO disc), a magnetic tape (MT), a random access memory (RAM), a compact disc (CD), a digital versatile disc (DVD), a secure digital card (SD card), or a universal serial bus memory (USB memory), a server, or the like can be used.

The processor 22 having the AD conversion unit 5, the image generation unit 6, the display controller 7, the measurement target recognition unit 9, the measurement unit 10, the measurement algorithm setting unit 12, and the apparatus controller 13 is configured of a central processing unit. (CPU) and a control program causing the CPU to execute various kinds of processing. However, the processor 22 may be configured using a field programmable gate array (FPGA), a digital signal processor (DSP), an application specific integrated circuit (ASIC), a graphics processing unit (CPU), or other integrated circuits (ICs) or may be configured by combining the IC circuits.

The AD conversion unit 5, the image generation unit 6, the display controller 7, the measurement target recognition unit 9, the measurement unit 10, the measurement algorithm setting unit 12, and the apparatus controller 13 of the processor 22 may be configured to be partially or wholly integrated into one CPU or the like.

Figure 3:
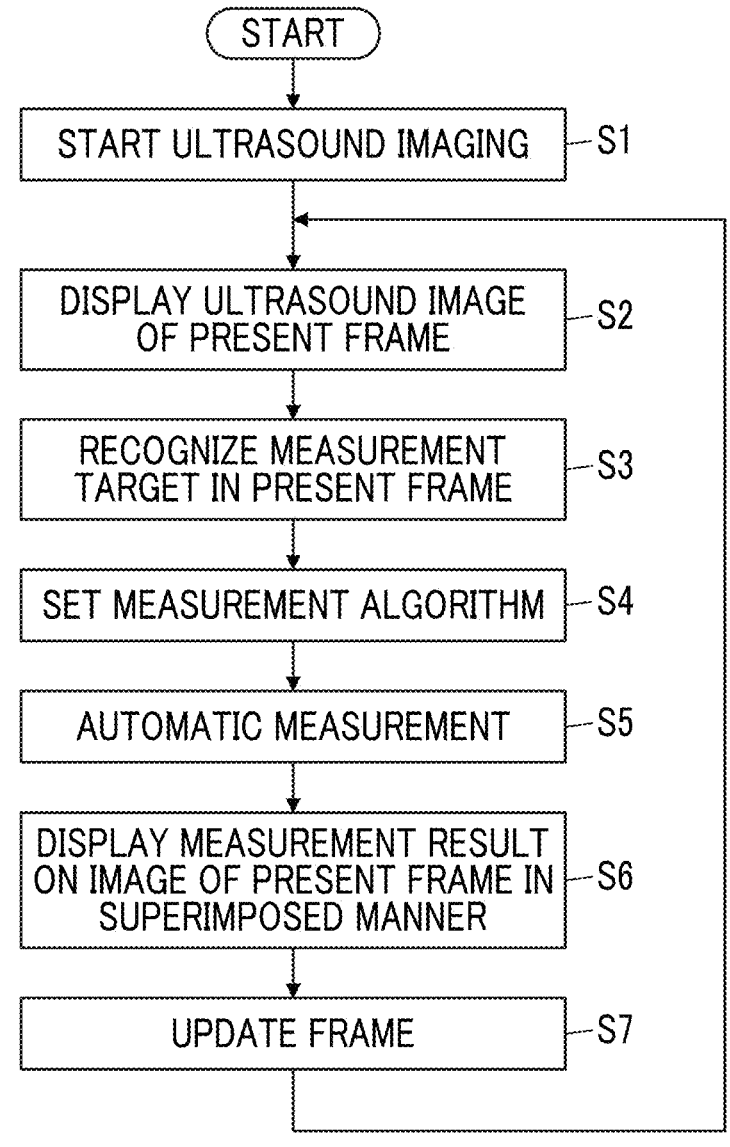
FIG. 3 is a flowchart showing the operation of the ultrasound diagnostic apparatus according to Embodiment 1 of the invention.

Next, the operation of the ultrasound diagnostic apparatus 1 of Embodiment 1 will be described referring to a flowchart shown in FIG. 3.

First, in Step S1, the ultrasound diagnostic apparatus 1 starts imaging of an ultrasound image according to an instruction from the user through the operating unit 15. In this case, the ultrasound probe 21 is operated by the user to be brought into contact with a body surface of the subject, and drive signals are sequentially supplied from the transmission unit 3 to the transducer array 2. Thereby, an ultrasonic beam is transmitted from the transducer array 2 into the subject. The reception unit 4 of the ultrasound probe 21 receives ultrasound echoes from the subject and converts the ultrasound echoes into reception signals, and the reception signals are processed by the AD conversion unit 5 and the image generation unit 6. Thereby, ultrasound images are sequentially generated. In the ultrasound diagnostic apparatus 1 of Embodiment 1, in a case where imaging of an ultrasound image is started in this manner, processing of subsequent Steps S2 to S7 is automatically executed.

Next, in Step S2, a latest ultrasound image generated by the image generation unit 6, that is, an ultrasound image of a present frame is displayed on the display unit 8 through the display controller 7.

In a case where the ultrasound image of the present frame is displayed on the display unit 8 in this manner, in Step S3, the measurement target recognition unit 9 automatically recognizes a measurement target included in the ultrasound image of the present frame.

Figure 4:
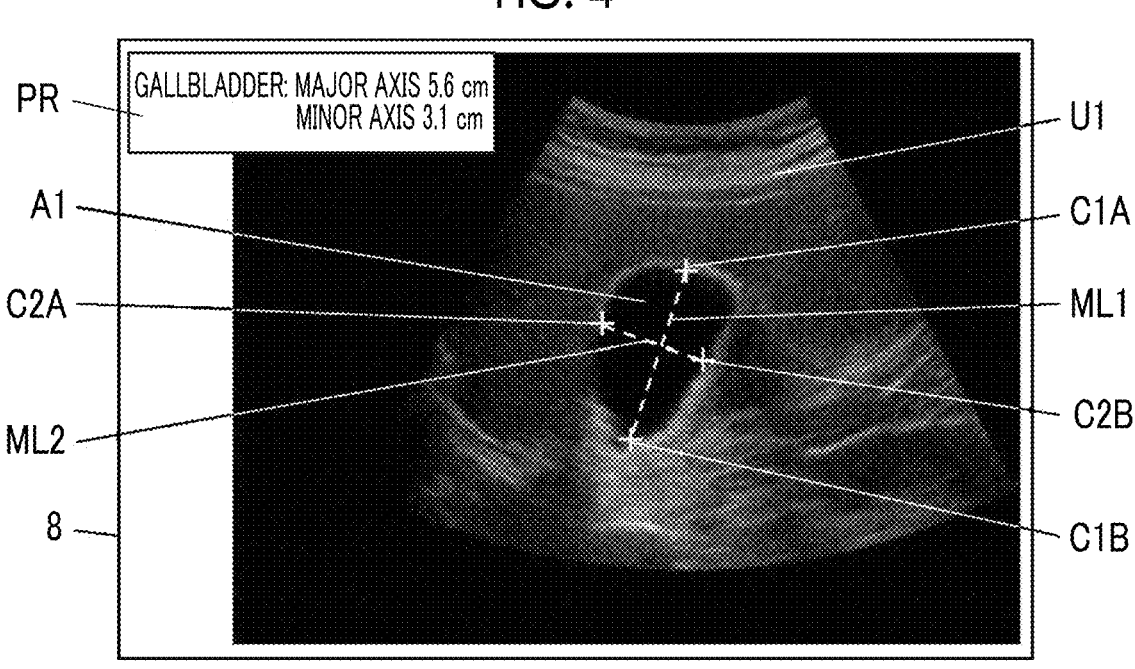
FIG. 4 is a diagram showing an example of a measurement result in Embodiment 1 of the invention.

In subsequent Step S4, the measurement algorithm setting unit 12 sets a measurement algorithm for the measurement target recognized in Step S3. For example, as shown in FIG. 4, in a case where the measurement target is the gallbladder A1, the measurement algorithm setting unit 12 sets a measurement algorithm that a line segment having a maximum distance with two points disposed on an inner wall of a region representing the gallbladder A1 in the ultrasound image U1 as end points is decided as a measurement line, and a length of the measurement line is measured. In the example shown in FIG. 4, a measurement line ML1 having calipers C1A and C1B as end points and a measurement line ML2, which is perpendicular to the measurement line ML1 and has calipers C2A and C2B as end points, are set in two directions perpendicular to each other such that a distance between two points on the inner wall of the gallbladder A1 is a maximum.

In this way, the measurement algorithm setting unit 12 sets the measurement algorithm according to the measurement target recognized in Step S3. In this case, the measurement algorithm setting unit 12 may set a measurement algorithm for measuring an area other than the measurement algorithm for measuring the length or may set a measurement algorithm for measuring both of the length and the area according to the measurement target.

In subsequent Step S5, the measurement unit 10 executes automatic measurement of the measurement target based on the measurement algorithm set in Step S4. For example, as shown in FIG. 4, the measurement unit 10 measures a length of the measurement line ML1 and a length of the measurement line ML2.

In a case where the measurement result is calculated in this manner, in Step S0, as shown in FIG. 4, the measurement unit 10 displays the calculated measurement result to be superimposed on the ultrasound image of the present frame. In this case, as shown in FIG. 4, the measurement unit 10 can display, as the measurement result, the measurement line ML having the calipers C1A and C1B as end points, the measurement line ML2 having the calipers C2A and C2B as end points, and a measurement result panel PR representing a name and a measurement value of the measurement target to be superimposed on the ultrasound image U1. The measurement result panel PR in FIG. 4 shows that the measurement target is the gallbladder A1, the length of the measurement line ML1, that is, a length in a major axis direction of the gallbladder A1 is 5.6 cm, and the length of the measurement line ML2, that is, a length in a minor axis direction of the gallbladder A1 is 3.1 cm.

In a case where the measurement result is displayed on the display unit 8 in this manner, measurement on the ultrasound image U1 of the present frame is completed, in Step S7, an ultrasound image on which measurement is to be executed is updated from the ultrasound image U1 of the present frame to an ultrasound image of a next frame, and the process returns to Step S2. In subsequent Steps S2 to S6, measurement of a measurement target is executed on the updated ultrasound image of the next frame, and in Step S7, an ultrasound image on which measurement is to be executed is updated to an ultrasound image of a subsequent frame. In this manner, the processing of Steps S2 to S7 is automatically executed sequentially on the ultrasound images of a plurality of continuous frames during imaging.

From the above, with the ultrasound diagnostic apparatus 1 of Embodiment 1, a series of operations of the display of the ultrasound image, the recognition of the measurement target, the setting of the measurement algorithm, the measurement of the measurement target, and the display of the measurement result is automatically executed sequentially on the ultrasound images of a plurality of continuous frames during imaging. Thus, for example, the user can very conveniently execute measurement on ultrasound images of a plurality of frames while searching for an optimum cross section for measurement of a measurement target.

Since the measurement results are sequentially displayed on the display unit 8 along with the ultrasound images, the user can search an optimum cross section of a measurement target while confirming a measurement result. With this, for example, even a user who is inexperienced in ultrasound diagnosis can easily acquire an ultrasound image including an optimum cross section of a measurement target and can exactly execute measurement.

In Embodiment 1, although the processing of subsequent Steps S3 to S7 is executed after the ultrasound image U1 of the present frame is displayed on the display unit 8 in Step S2, the ultrasound image U1 of the present frame can be displayed on the display unit 8 at any timing in Steps S3 to S6. For example, the display of the ultrasound image U1 in Step S2 and the display of the measurement result in Step S6 may be performed simultaneously.

In Embodiment 1, although an example where the measurement target is included in the ultrasound image U1 of the present frame has been described, a measurement target may not be included in the ultrasound image U1. In this case, a measurement target cannot be recognized in Step S3. Thus, for example, immediately after the ultrasound image of the present frame is displayed in Step S2, Steps S4 to S6 can be omitted, and frame update can be performed in Step S7.

In Embodiment 1, although, in a case where imaging of an ultrasound image is started in Step S1 according to an instruction from the user through the operating unit 15, the processing of Steps S2 to S7 is automatically executed sequentially on the ultrasound image of a plurality of continuous frames during imaging, the operation of the ultrasound diagnostic apparatus 1 can be ended according to an instruction from the user through the operating unit 15. For example, the operations of Steps S2 to S7 can be ended by ending imaging of an ultrasound image according to an instruction from the user through the operating unit 15. In this case, for example, the instruction from the user through the operating unit 15 can be issued at any timing in Steps S2 to S7, and the operation of the ultrasound diagnostic apparatus 1 can be ended.

Although the measurement algorithm setting unit 12 automatically sets the measurement algorithm according to the measurement target recognized in Step S3, the measurement algorithm to be set can be set to a measurement algorithm conforming to a user's preference or the like in advance. For example, as shown in FIG. 4, a first measurement algorithm for measuring both of the length in the major axis direction, that is, the length of the measurement line ML1 and the length in the minor axis direction, that is, the length of the measurement line ML2, a second measurement algorithm for measuring only the length of the measurement line ML1 in the major axis direction, and a third measurement algorithm for measuring only the length of the measurement line ML2 in the minor axis direction are prepared for the gallbladder A1, and the user is prompted to select one of the three measurement algorithms in advance through the operating unit 15. Thereby, it is possible to set the measurement algorithm for the gallbladder A1 to the measurement algorithm conforming to the user's preference.

In displaying the measurement result on the display unit 8, in a case where a plurality of measurement values are calculated, the measurement unit 10 can display a plurality of measurement values, names of a plurality of corresponding measurement targets, a plurality of corresponding measurement lines, a plurality of corresponding calipers, and the like in different aspects for the respective measurement values. For example, the measurement unit 10 can display each measurement value on the display unit 8 by making at Least one of a color, a thickness, a kind of a line, such as a solid line or a broken line, or transmittance of an item related to each measurement value different.

In Embodiment 1, although an example where only one measurement target is included in the ultrasound image U1 of the present frame, and the measurement of the one measurement target is executed has been described, in a case where a plurality of measurement targets are included in the ultrasound image of the present frame, measurement of a plurality of measurement targets may be executed.

Figure 5:
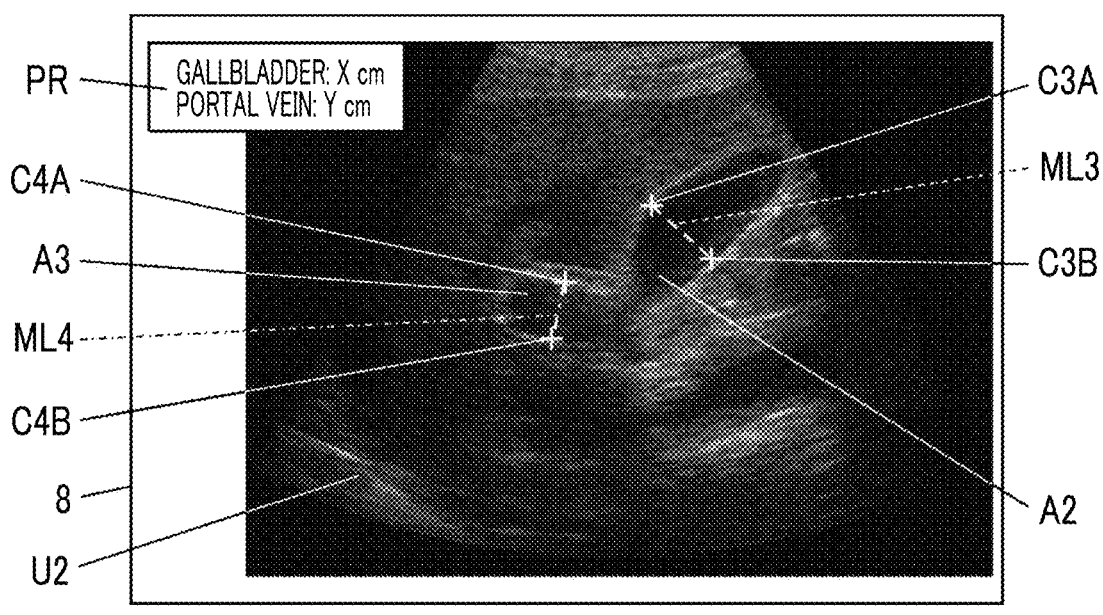
FIG. 5 is a diagram showing an example of a measurement result in a modification example of Embodiment 1 of the invention.

For example, as shown in FIG. 5, in a case where two measurement targets of a gallbladder A2 and a portal vein A3 are included in an ultrasound image U2 of a present frame, in Step S3, the gallbladder A2 and the portal vein A3 are recognized as measurement targets by the measurement target recognition unit 9. Next, measurement algorithms corresponding to the gallbladder A2 and the portal vein A3 recognized in Step S3 are set measurement algorithm setting unit 12 in Step S4.

In a case where the measurement algorithms corresponding to the gallbladder A2 and the portal vein A3 are set in this manner, measurement of the gallbladder A2 and measurement of the portal vein A3 are executed in Step S5 and a measurement result of the gallbladder A2 and a measurement result of the portal vein A3 are displayed to be superimposed on the ultrasound image U2 of the present frame as shown in FIG. 5 in Step S6 by the measurement unit 10. In the example shown in FIG. 5, as the measurement results, a pair of calipers C3A and C3B disposed on an inner wall of the gallbladder A2, a measurement line ML3 with a pair of calipers C3A and C3B as end points, a pair of calipers C4A and C4B disposed on an inner wall of the portal vein A3, a measurement line MF 4 with a pair of calipers C4A and C4B as end points, and a measurement result panel PR are displayed. The measurement result panel PR shows that the measurement targets are the gallbladder A2 and the portal vein A3, a measurement value of the gallbladder A2 is X cm, and a measurement value of the portal vein. A3 is Y cm.

In this manner, when measurement of a plurality of measurement targets is executed, for example, measurement can be executed in compliance with a determined order. For example, any one point on the ultrasound image U2 can be set as the origin, and measurement can be executed in order from the measurement target close to the origin.

Here, as the ultrasound probe 21 is operated by the user and the ultrasound probe 21 moves on the body surface of the subject, a new measurement target different from a measurement target first recognized after imaging of an ultrasound image is started appears in the ultrasound image. In this ease, the ultrasound diagnostic apparatus 1 can execute measurement of only the existing measurement target without executing measurement of the newly added measurement target. With this, it is possible to execute measurement of only a measurement target intended by the user, and to reduce a calculation load in the ultrasound diagnostic apparatus 1.

For example, measurement of a measurement target newly appearing in the ultrasound image may be executed similarly to a measurement target already recognized at the beginning of imaging. For example, after a new measurement target different from the measurement target already recognized appears in the ultrasound image, the ultrasound diagnostic apparatus 1 can start measurement of the newly added measurement target with an instruction from the user through the operating unit 15 as a trigger. With this, it is possible to execute measurement more conforming to the intention of the user.

Embodiment 2

In Embodiment 1, the user determines whether or not the ultrasound image of the present frame includes the optimum cross section of the measurement target. In contrast, the determination may be automatically performed by the ultrasound diagnostic apparatus.

Figure 6:
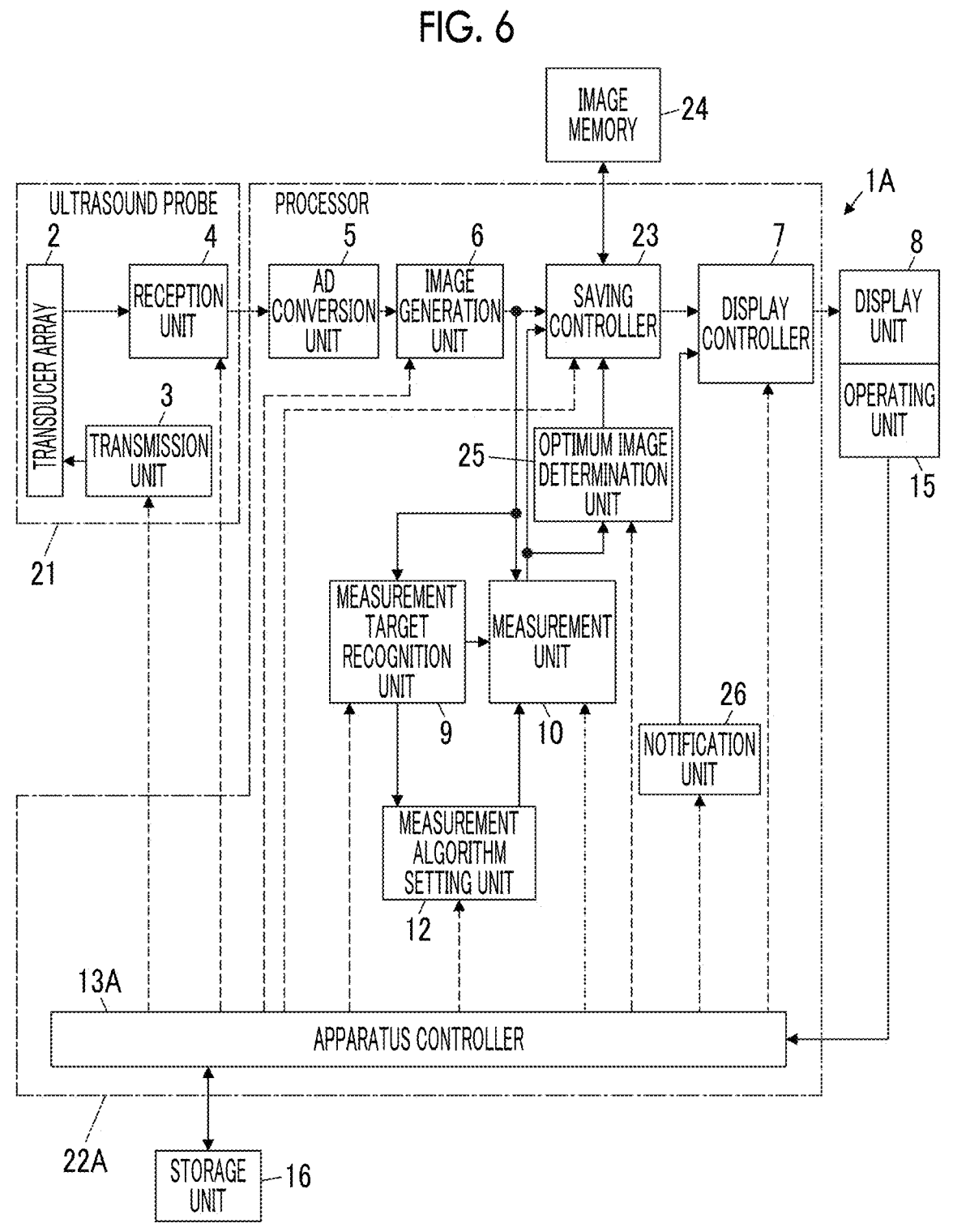

FIG. 6 shows the configuration of an ultrasound diagnostic apparatus 1A according to Embodiment 2. The ultrasound diagnostic apparatus 1A of Embodiment 2 comprises an apparatus controller 13A instead of the apparatus controller 13 in the ultrasound diagnostic apparatus 1 of Embodiment 1 shown in FIG. 1, and further comprises a saving controller 23, an image memory 24, an optimum image determination unit 25, and a notification unit 26.

In the ultrasound diagnostic apparatus 1A of Embodiment 2, the saving controller 23, the display controller 7, and the display unit 8 are sequentially connected to the image generation unit 6, and the image memory 24 is connected to the saving controller 23. The measurement unit 10 and the optimum image determination unit 25 are connected to the saving controller 23, and the optimum image determination unit 25 is connected to the measurement unit 10. The notification unit 26 is connected to the display controller 7.

The apparatus controller 13A is connected to the transmission unit 3, the reception unit 4, the image generation unit 6, the display controller 7, the measurement target recognition unit 9, the measurement unit 10, the measurement algorithm setting unit 12, the operating unit 15, the storage unit 16, the saving controller 23, the optimum image determination unit 25, and the notification unit 26. The AD conversion unit 5, the image generation unit 6, the display controller 7, the measurement target recognition unit 9, the measurement unit 10, the measurement algorithm setting unit 12, the apparatus controller 13A, the saving controller 23, the optimum image determination unit 25, and the notification unit 26 configure a processor 22A.

The optimum image determination unit 25 of the processor 22A determines whether or not an ultrasound image of a present frame among a plurality of continuous frames during imaging includes an optimum cross section of a measurement target, that is, whether or not the ultrasound image of the present frame is an optimum image. In this case, the optimum image determination unit 25 can determine that the ultrasound image of the present frame includes the optimum image, for example, in a case where a measurement value in the ultrasound image of the present frame among measurement values of a length, an area, and the like calculated by the measurement unit 10 for the measurement targets included in the ultrasound images of a plurality of continuous frames during imaging is a maximum. The optimum image determination unit 25 may determine that the ultrasound image of the present frame is the optimum image in a case where the likelihood in the ultrasound image of the present frame among the likelihood calculated by the measurement target recognition unit 9 for the measurement targets included in the ultrasound images of a plurality of continuous frames during imaging is a maximum.

The image memory 24 of the ultrasound diagnostic apparatus 1A saves the ultrasound images, the measurement results, and the like, and similarly to the storage unit 16, a recording medium, such as an HDD, an SSD, an FD, an MO disc, an MT, a RAM, a CD, a DVD, an SD card, or a USB memory, a server, or the like can be used.

The saving controller 23 of the processor 22A saves the ultrasound image of the present frame and the measurement result obtained by the measurement unit 10 for the ultrasound image of the present frame in the image memory 24 each time the optimum image determination unit 25 determines that the ultrasound image of the present frame is the optimum image. In this case, for example, the saving controller 23 can overwrite and save the optimum image and the measurement result in the image memory 24. For example, the saving controller 23 may add and save the optimum image and the measurement result in the image memory 24.

Figure 7:
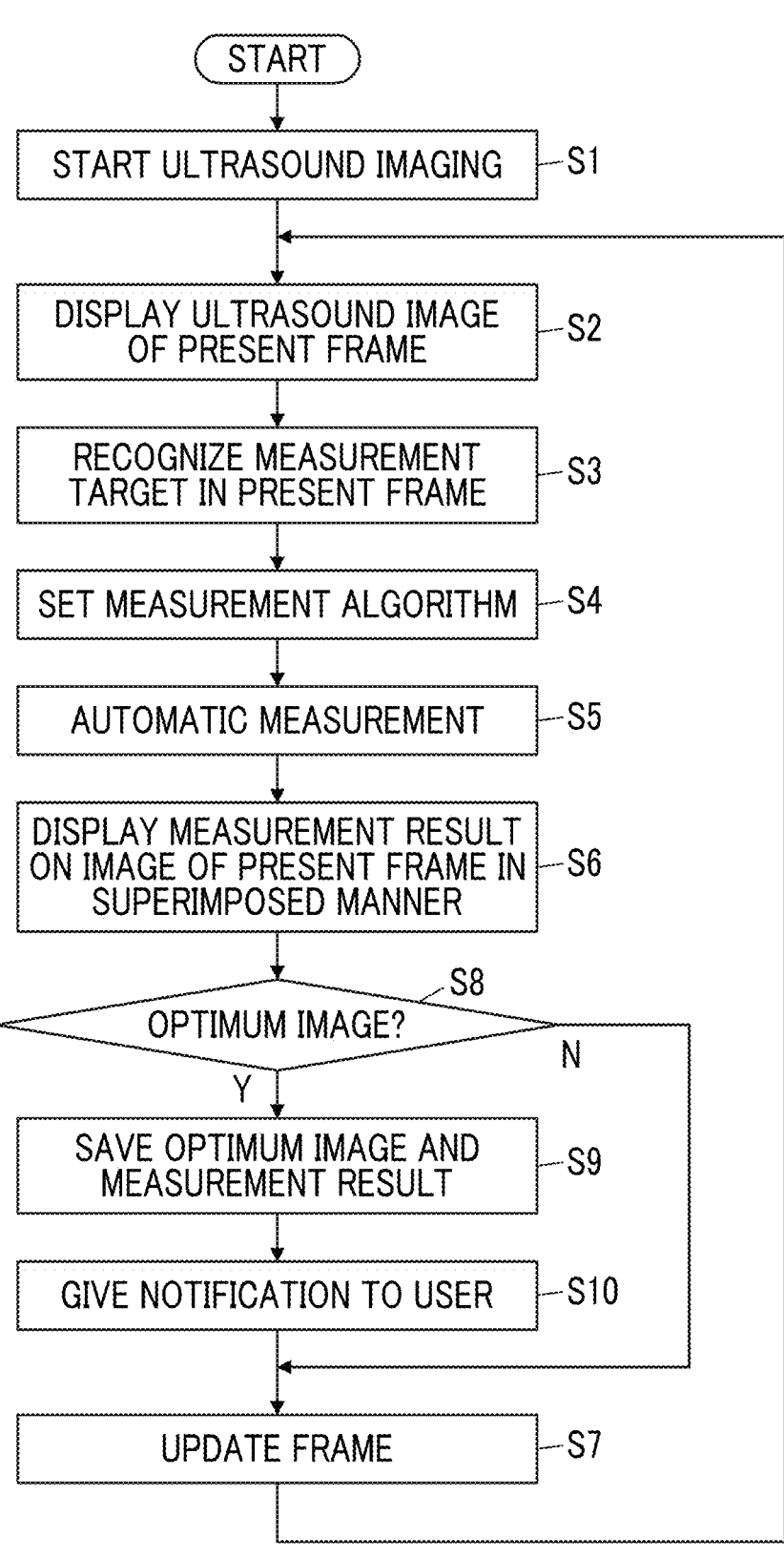
FIG. 7 is a flowchart showing the operation of the ultrasound diagnostic apparatus according to Embodiment 2 of the invention.

Next, the operation of the ultrasound diagnostic apparatus 1A of Embodiment 2 will be described referring to a flowchart shown in FIG. 7. The flowchart of FIG. 7 provides Steps S8 to S10 between Steps S6 and S7 in the flowchart shown in FIG. 3.

First, in Step S1 the ultrasound diagnostic apparatus 1A starts imaging of an ultrasound image according to an instruction from the user through the operating unit 15. In the ultrasound diagnostic apparatus 1A of Embodiment 2, in a case where imaging of an ultrasound image is started in this manner, processing of subsequent Steps S2 to S6, S8 to S10, and S7 is automatically executed.

In a case where an ultrasound image of a present frame is generated, in Step S2, the ultrasound image of the present frame is displayed on the display unit 8.

In subsequent Step S3, a measurement target included in the ultrasound image of the present frame is recognized by the measurement target recognition unit 9. In Step S4, a measurement algorithm is set based on the measurement target recognized in this manner by the measurement algorithm setting unit 12.

In Step S5, measurement of the measurement target recognized in Step S3 is executed based on the measurement algorithm set in Step S4 by the measurement unit 10.

In Step S6, as shown in FIG. 4, the measurement unit 10 displays a measurement result obtained in Step S5 to be superimposed on the ultrasound image of the present frame.

In subsequent Step S8, the optimum image determination unit 25 determines whether or not the ultrasound image of the present frame includes an optimum cross section for the measurement of the measurement target, that is, whether or not the ultrasound image of the present frame is an optimum image. In this case, the optimum image determination unit 25 determines that the ultrasound image of the present frame is the optimum image, for example, in a case where the measurement value in the ultrasound image of the present frame obtained in Step S5 among the measurement values in a plurality of continuous frames during imaging is a maximum.

In Step S8, in a case where the optimum image determination unit 25 determines that the ultrasound image of the present frame is not the optimum image, measurement in the ultrasound image of the present frame is completed, and the process progresses to Step S7. In Step S7, a frame on which measurement is to be executed is updated to a next frame, and the process returns to Step S2.

In a case where the optimum image determination unit 25 determines that the ultrasound image of the present frame is the optimum image, the process progresses to Step S9.

In Step S9, the saving controller 23 saves the ultrasound image of the present frame and the measurement result in the image memory 24. In this manner, the optimum image is saved in the image memory 24, whereby the user can confirm the optimum image and the measurement result saved in the image memory 24 after ultrasound diagnosis ends.

Figure 8:
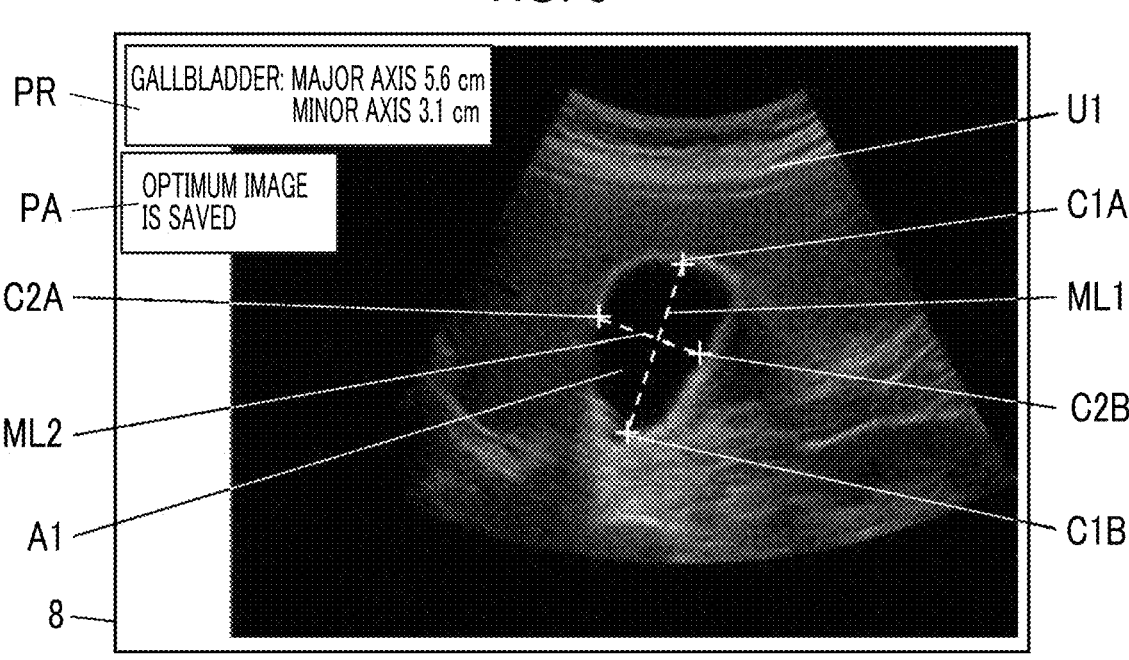
FIG. 8 is a diagram showing an example of notification in Embodiment 2 of the invention.

In subsequent Step S10, the notification unit 26 notifies the user that the optimum image is saved. In this case, for example, as shown in FIG. 8, the notification unit 26 can display a notification panel PA representing saving of the optimum image on the display unit 8 through the display controller 7.

Though not shown, for example, a sound generation unit comprising a speaker or the like configured to generate sound may be provided in the ultrasound diagnostic apparatus 1A, and the notification by the notification unit 26 may be given to the user as sound through the sound generation unit.

In this manner, in a case where the notification of Step S10 is completed, the measurement in the ultrasound image of the present frame is completed, and the process progresses to Step S7. In Step S7, a frame on which measurement is to be executed is updated to a next frame, and the process returns to Step S2.

In subsequent Steps S2 to S6, the display of the ultrasound image, the recognition of the measurement target, the setting of the measurement algorithm, the automatic measurement of the measurement target, and the display of the measurement result are performed for the updated frame, and in Step S8, the optimum image determination unit 25 determines whether or not the ultrasound image of the updated frame is an optimum image. In Step S8, in a case where the optimum image determination unit 25 determines that the ultrasound image of the updated frame is not an optimum image, the measurement in the ultrasound image of the updated frame is completed, and in Step S7, a frame on which measurement is to be executed is updated to a next frame.

In Step S8, in a case where the optimum image determination unit 25 determines that the ultrasound image of the updated frame is an optimum image, the process progresses to Step S9, and the ultrasound image of the updated frame and the measurement result are saved in the image memory 24 by the saving controller 23. In this case, the saving controller 23 may overwrite and save, as the optimum image and the measurement result, the ultrasound image of the updated frame and the measurement result in the image memory 24 or may add and save, as the optimum image and the measurement result, the ultrasound image of the updated frame and the measurement result in the image memory 24. In Step S9, in a case where the optimum image and the measurement result are saved, in Step S10, the notification unit 26 gives notification that the optimum image is saved.

With this, the measurement in the ultrasound image of the updated frame is completed, and in Step S7, a frame on which measurement is to be executed is updated to a next frame.

In this manner, the processing of Steps S2 to S7 is repeated, a plurality of ultrasound images and the measurement results are displayed sequentially on the display unit 8, and the ultrasound image determined to be an optimum image by the optimum image determination unit 25 and the measurement result are saved in the image memory 24.

From the above, with the ultrasound diagnostic apparatus 1A of Embodiment 2, the optimum image including the optimum cross section of the measurement target for the measurement is determined by the optimum image determination unit 25, and the optimum image and the measurement result are automatically saved in the image memory 24 by the saving controller 23. Thus, in particular, even a user who is inexperienced in ultrasound diagnosis can acquire an optimum image and can execute exact measurement.

In Embodiment 2, white the length in the major axis direction of the gallbladder A1, that is, the length of the measurement line MLA and the length in the minor axis direction of the gallbladder A1, that is, the length of the measurement line ML2 are calculated as the measurement values by the measurement unit 10, in this case, the optimum image determination unit 25 may determine, as an optimum image, an ultrasound image of a frame where the length of the measurement line ML1 is a maximum or may determine, as an optimum image, an ultrasound image of a frame where the length of the measurement line ML2 is a maximum. In this way, in a case where a plurality of measurement values are acquired for one measurement target, the optimum image determination unit 25 can determine, as an optimum image, an ultrasound image of a frame where one measurement value among a plurality of measurement values is a maximum.

For each of a plurality of measurement values, the optimum image determination unit 25 may determine, as an optimum image, a frame where the measurement value is a maximum. In this case, for each of a plurality of measurement values, the saving controller 23 can save the optimum image and the measurement result in the image memory 24.

In Embodiment 2, although the gallbladder A1 is included as only one measurement target in the ultrasound image U1 of the present frame, a plurality of measurement targets may be included in the ultrasound image of the present frame. In this case, the optimum image determination unit 25 can determine the optimum image for each of a plurality of measurement targets, and the saving controller 23 can save the optimum image and the measurement result of each of a plurality of measurement targets in the image memory 24.

Figure 9:
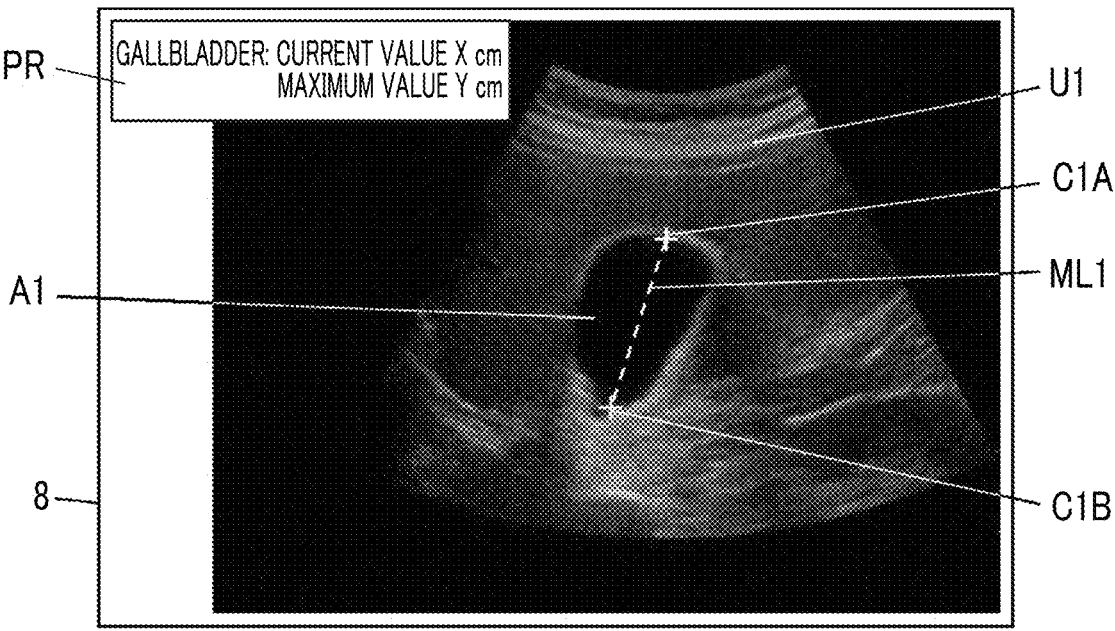
FIG. 9 is a diagram showing an example of a measurement result in a modification example of Embodiment 2 of the invention.

In Embodiment 2, although only the measurement result in the ultrasound image U1 of the present frame is displayed to be superimposed on the ultrasound image of the present frame, for example, as shown in FIG. 9, the saving controller 23 may display the measurement value in the optimum image along with the measurement result in the ultrasound image of the present frame. In the example shown in FIG. 9, a measurement result panel PR indicating that the measurement target is the gallbladder, the measurement value in the ultrasound image of the present frame is X cm, and the measurement value in the optimum image, that is, a maximum value of the measurement value at the present time is Y cm is displayed to be superimposed on the ultrasound image U1. In this way, the measurement result in the ultrasound image of the present frame and the measurement result in the optimum image are displayed to be superimposed on the ultrasound image 111 of the present frame, whereby the user can confirm how much the ultrasound image IR of the present frame and the optimum image are different through the measurement results.

In Embodiment 2, although determination is made in Step S8 that the ultrasound image of the present frame is the optimum image in a case where the measurement value obtained in Step S5 is a maximum, determination may be made that the ultrasound image of the present frame is the optimum image in a case where the likelihood calculated in Step S3 by the measurement target recognition unit 9 is a maximum. In this case, a series of operations of Steps S8 to S10 can be executed at any timing in Steps S3 to S7. For example, the series of operations of Steps S8 to S10 can be executed at a timing between Steps S3 and S4.

In Step S8, the optimum image determination unit 25 may determine that the ultrasound image of the present frame is the optimum image in a case where the measurement value obtained in Step S5 is a minimum. For example, in a case where a measurement target included in the ultrasound image is a part of which the size changes cyclically due to pulsation or the like, the optimum image determination unit 25 can determine, as the optimum image, the ultrasound image of the present frame where a measurement value of an inner diameter or the like is a minimum.

Embodiment 3

In Embodiment 2, the ultrasound image determined to be the optimum image by the optimum image determination unit 25 is saved in the image memory 24 by the saving controller 23. In contrast, ultrasound images of a plurality of frames during imaging may be saved in the image memory 24, and the saved ultrasound images of a plurality of frames may be displayed on the display unit 8. Here, an ultrasound diagnostic apparatus according to Embodiment 3 is the same as the ultrasound diagnostic apparatus 1A of Embodiment 2 shown in FIG. 6.

In Embodiment 3, for example, the saving controller 23 saves, not just the optimum image, ultrasound images of all frames captured in the past a determined time from the present frame among a plurality of continuous frames during imaging and measurement results in the image memory 24. In this case, the saving controller 23 can save the ultrasound image of the frame determined to be the optimum image by the optimum image determination unit 25 in the image memory 24 while providing a flag.

Figure 10:
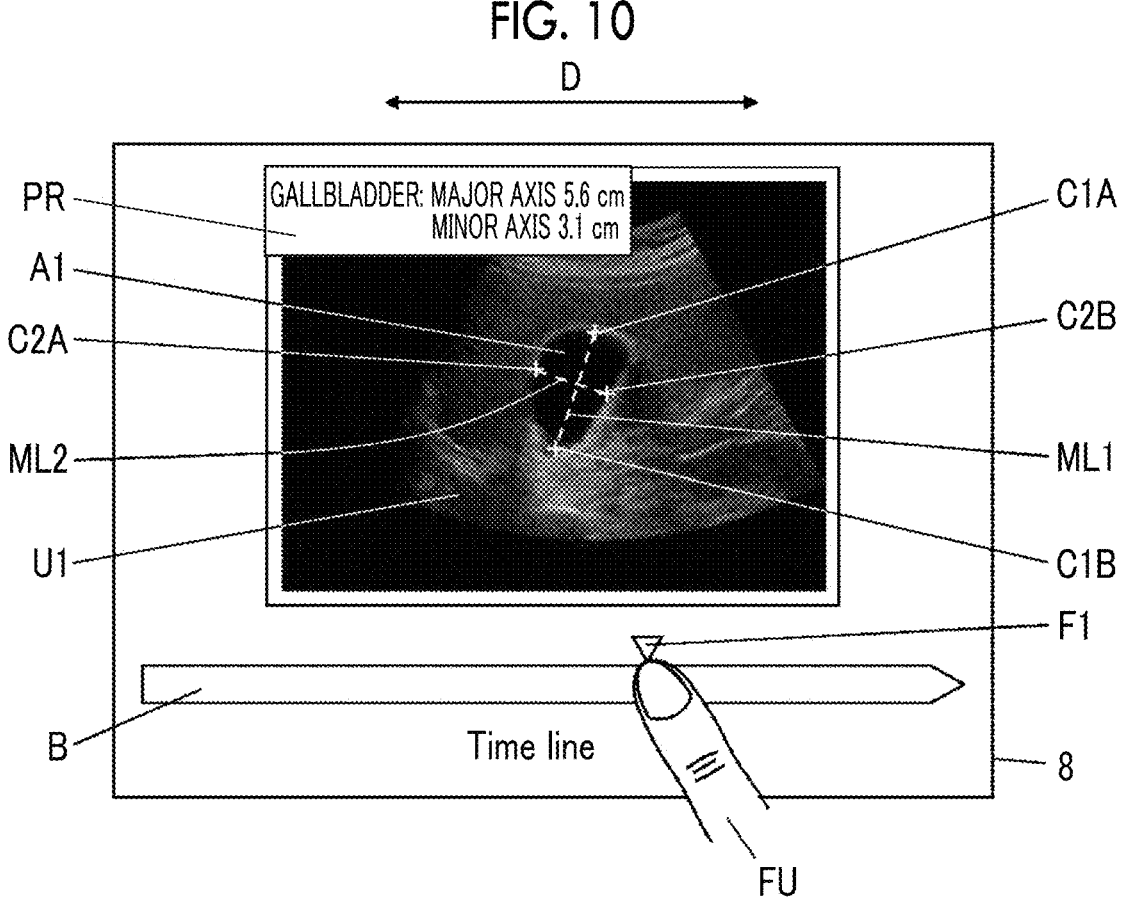
FIG. 10 is a diagram showing an example of a selected ultrasound image in Embodiment 3 of the invention.

For example, as shown in FIG. 10, the saving controller 23 can display the ultrasound images of a plurality of frames and the measurement results saved in the image memory 24 on the display unit 8. Here, the saving controller 23 can execute a display aspect shown in FIG. 10, for example, with issuance of an instruction from the user through the operating unit 15 as a trigger. In the example shown in FIG. 10, an ultrasound image U1 that is determined to be an optimum image by the optimum image determination unit 25 and includes a gallbladder A1 as a measurement target, calipers C1A, C1B, C2A, and C2B that are measurement results in the ultrasound image U1, measurement lines ML1 and ML2, a measurement result panel PR, a display bar B extending along one direction, and a flag mark F1 disposed in the vicinity of the display bar B are displayed on the display unit 8.

Here, for description, it is assumed that the optimum image determination unit 25 determines, as an optimum image, an ultrasound image of a frame where the length in the major axis direction of the gallbladder A1, that is, the length of the measurement line ML1 is a maximum. Furthermore, as shown in FIG. 10, it is assumed that the display bar B extends right and left along a lateral direction D.

A position of each point of the display bar B in the lateral direction D corresponds to the ultrasound images of a plurality of frames saved in the image memory 24, and for example, in a case where the display bar B is touched with a finger FU of the user, an ultrasound image of a frame corresponding to the touch position on the display bar B is displayed on the display unit 8. The position of the display bar B corresponds to an ultrasound image of a new frame toward the right, and corresponds to an ultrasound image of an old frame toward the left. In the example shown in FIG.

10, the position of the display bar B corresponding to the ultrasound image U1 as the optimum image is touched with the finger FU of the user, and the ultrasound image U1 and the measurement result are displayed on the display unit 8.

The flag mark F1 corresponds to the flag provided to the optimum image by the saving controller 23, and is a mark indicating the position on the display bar B corresponding to the optimum image. In this way, the flag mark F1 is displayed on the display unit 8 corresponding to the position on the display bar B, whereby the user can easily select an optimum image among the ultrasound images of a plurality of frames saved in the image memory 24 and can display the optimum image on the display unit 8.

From the above, with the ultrasound diagnostic apparatus of Embodiment 3, the saving controller 23 provides the flag to the optimum image and saves the ultrasound images of all frames captured in the past the determined time from the present frame among a plurality of continuous frames during imaging and the measurement results in the image memory 24, and as shown in FIG. 10, when the ultrasound images of a plurality of frames are selected and displayed, the flag mark F1 representing the optimum image is displayed. Thus, the user can easily browse all of the ultrasound images of a plurality of frames saved in the image memory 24, can easily select the optimum image, and can display the optimum image on the display unit 8.

In Embodiment 3, although the optimum image determination unit 25 determines, as the optimum image, the ultrasound image of the frame where the length in the major axis direction of the gallbladder A1, that is, the length of the measurement line ML1 is a maximum, for example, an ultrasound image of a frame where the length in the minor axis direction of the gallbladder A1, that is, the length of the measurement line ML2 is a maximum can be determined as an optimum image. In this case, the saving controller 23 can provide a flag to the ultrasound image of the frame where the length of the measurement line ML2 is a maximum, and can display a new flag mark (not shown) in the vicinity of the display bar B. In this way, in a case where a plurality of measurement values are acquired for one measurement target, the optimum image determination unit 25 can perform determination of an optimum image for each of a plurality of measurement values, and the saving controller 23 can provide a flag to an ultrasound image of a frame determined to be an optimum image for each of a plurality of measurement values. In this case, the saving controller 23 can display flag marks on the display unit 8 in different display aspects, such as shape or color, for a plurality of measurement values.

In Embodiment 3, although the gallbladder A1 as only one measurement target is included in the ultrasound image U1, a plurality of measurement targets may be included. In this case, the optimum image determination unit 25 can perform determination of an optimum image for each of a plurality of measurement targets, and the saving controller 23 can provide a flag to an ultrasound image of a frame determined to be an optimum image for each of a plurality of measurement targets. In this case, the saving controller 23 can display flag marks on the display unit 8 in different display aspects, such as shape or color, for the respective measurement targets.

In Embodiment 3, although an example where the optimum image determination unit 25 determines that the measurement value of the ultrasound image of the frame where the length in the major axis direction of the gallbladder A1, that is, the length of the measurement limbo ML1, or the like is a maximum is the optimum image has been described, the optimum image determination unit 25 may determine that the ultrasound image of the frame where the likelihood of the measurement target calculated by the measurement target recognition unit 9 is a maximum is an optimum image. In this case, the saving controller 23 can save, in the image memory 24, the optimum image where the likelihood of the measurement target is a maximum, while providing a flag.

For example, the optimum image determination unit 25 may determine that an ultrasound image of a frame where a measurement value obtained by the measurement unit 10 is a minimum is an optimum image. In this case, the saving controller 23 can save, in the image memory 24, the optimum image where the measurement value is a minimum, while providing a flag.

Embodiment 4

Figure 11:
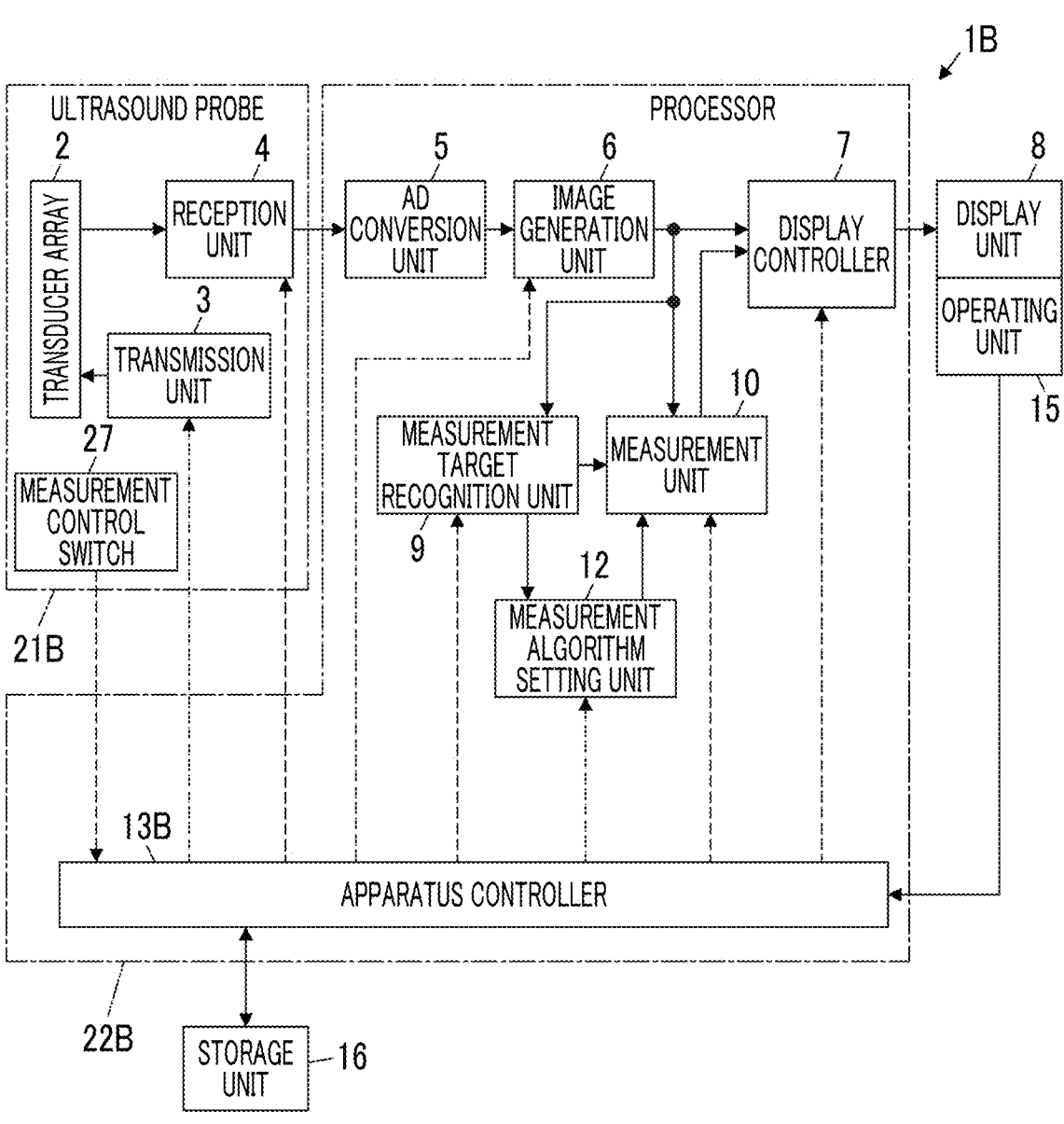
FIG. 11 is a diagram showing the configuration of an ultrasound diagnostic apparatus according to Embodiment 4 of the invention.

FIG. 11 shows the configuration of an ultrasound diagnostic apparatus 1B according to Embodiment 4. The ultrasound diagnostic apparatus 1B of Embodiment 4 comprises an apparatus controller 13B instead of the apparatus controller 13 in the ultrasound diagnostic apparatus 1 of Embodiment 1 shown in FIG. 1, and comprises an ultrasound probe 21B where a measurement control switch 27 is provided, instead of the ultrasound probe 21.

In the ultrasound diagnostic apparatus 1B of Embodiment 4, the ultrasound probe 21B is provided with the measurement control switch 27. The apparatus controller 13B is connected to the transmission unit 3, the reception unit 4, the image generation unit 6, the display controller 7, the measurement target recognition unit 9, the measurement unit 10, the measurement algorithm setting unit 12, the operating unit 15, the storage unit 16, and the measurement control switch 27.

The AD conversion unit 5, the image generation unit 6, the display controller 7, the measurement target recognition unit 9, the measurement unit 10, the measurement algorithm setting unit 12, and the apparatus controller 13B configure a processor 22B.

The measurement control switch 27 of the ultrasound probe 21B is a switch that is operated by the user to perform a command to start and a command to end a series of measurement operations including the recognition of the measurement target by the measurement target recognition unit 9, the setting of the measurement algorithm by the measurement algorithm setting unit 12, and the measurement of the measurement target by the measurement unit 10. In a case where the measurement control switch 27 is operated by the user, the command to start and the command to end the series of measurement operations are sent to the apparatus controller 13B, and the series of measurement operations is started or ended under the control of the apparatus controller 13B.

More specifically, for example, the measurement control switch 27 can be configured of a push button switch attached to a casing of the ultrasound probe 21B, and the user can start the series of measurement operations by pushing the measurement control switch 27. While the measurement control switch 27 is continuously pushed by the user, the series of measurement operations is sequentially performed, and the user can end the series of measurement operations by releasing the measurement control switch 27.

From the above, with the ultrasound diagnostic apparatus 1B according to Embodiment 4, the user can easily perform the command to start and the command to end the series of measurement operations by operating the measurement control switch 27 provided in the ultrasound probe 21B. Thus, for example, the user can easily perform control such that the ultrasound diagnostic apparatus 1B performs the series of measurement operations only when an intended measurement target appears in the ultrasound image of the present frame, thereby reducing a calculation load of the ultrasound diagnostic apparatus 1B.

For example, even though the series of measurement operations is performed only for a measurement target in an ultrasound image when measurement is started, when an intended measurement part appears in the ultrasound image of the present frame, the user operates the measurement control switch 27 and the series of measurement operation is started again. Thus, it is possible to reliably measure an intended measurement target.

In Embodiment 4, although an example where the measurement control switch 27 is configured of the button has been described, the configuration of the measurement control switch 27 is not limited thereto. For example, the measurement control switch 27 can have any configuration in which a switching operation can be performed, such as a slide switch, a toggle switch, a locker switch, or a touch switch.

In Embodiment 4, although the measurement control switch 27 is provided in the ultrasound probe 21B, the measurement control switch 27 is not particularly limited as being provided in the ultrasound probe 21B. For example, the ultrasound diagnostic apparatus 1B may have a casing including the processor 22B and the like, and the measurement control switch 27 may be provided in the casing of the ultrasound diagnostic apparatus 1B. However, it is preferable that the measurement control switch 27 is provided in the ultrasound probe 21B from a viewpoint of easiness of an operation.

In Embodiments 1 to 4, although the operating unit 15 comprises the touch sensor, the configuration of the operating unit 15 is not limited thereto. For example, as the operating unit 15, an interface through which the user performs an input operation, such as a keyboard, a mouse, or a trackball, can be used.

In Embodiments 1 to 4, although the measurement of the measurement target is executed based on the ultrasound image, measurement of a measurement target can be executed on an acoustic wave image other than an ultrasound image. For example, though not shown, a so-called photoacoustic wave probe can be configured by providing a laser source generating a so-called photoacoustic wave image in the ultrasound diagnostic apparatuses of Embodiments 1 to 4, and the transducer array 2 of the photoacoustic wave probe can be prompted to receive acoustic waves from the subject resulting from laser light to generate a photoacoustic wave image.

In this manner, measurement of a measurement target can be executed on an ultrasound image, a photoacoustic wave image, and a composite image, in which an ultrasound image and a photoacoustic wave image are superimposed, using an ultrasound probe and an acoustic wave probe, such as a photoacoustic wave probe.

EXPLANATION OF REFERENCES 1, 1A, 1B: ultrasound diagnostic apparatus
2: transducer array
3: transmission unit
4: reception unit
5: AD conversion unit
6: image generation unit
7: display controller 8: display unit
9: measurement target recognition unit
10: measurement unit
12: measurement algorithm setting unit
13, 13A, 13B: apparatus controller
15: operating unit
16: storage unit
17: signal processing unit
18: DSC
19: image processing unit
21: ultrasound probe
22, 22A, 22B: processor
23: saving controller
24: image memory
25: optimum image determination unit
26: notification unit
27: measurement control switch
A1, A2: gallbladder
A3: portal vein
B: display bar
C1A, C1B, C2A, C2B, C3A, C3B, C4A, C4B: caliper
D: lateral direction
F1: flag mark
EU: finger
ML2, ML3, ML4: measurement line
PA: notification panel
PR: measurement result panel
U1, U2: ultrasound image

What is claimed is:

1. An acoustic wave diagnostic apparatus that sequentially displays acoustic wave images of a plurality of continuous frames during imaging on a display monitor, the acoustic wave diagnostic apparatus comprising:
   an image memory; and
   a processor configured to
      store measurement algorithms corresponding to a plurality of predetermined organs,
      automatically discriminate a type of a measurement target included in an acoustic wave image of a present frame displayed on the display monitor, as one organ among the plurality of predetermined organs, by using a machine learning,
      automatically select and set a measurement algorithm corresponding to the one organ among the measurement algorithms,
      measure the measurement target based on the measurement algorithm corresponding to the one organ and display a measurement result on the display monitor to be superimposed on the acoustic wave image of the present frame,
      determine whether or not the acoustic wave image of the present frame among the plurality of continuous frames during imaging includes an optimum cross section of the measurement target, and
      save the acoustic wave image of the present frame which is determined to include the optimum cross section and the measurement result corresponding to the present frame to the image memory by overwriting the acoustic wave image and the measurement result which have been already saved in the image memory.

2. The acoustic wave diagnostic apparatus according to claim 1, further comprising:
   an operating device through which a user performs an input operation, wherein the processor is further configured to display the acoustic wave image saved in the image memory on the display monitor based on a user's operation through the operating device.

3. The acoustic wave diagnostic apparatus according to claim 2,
wherein the processor is further configured to add and save the acoustic wave image of the present frame which is determined to include the optimum cross section and the measurement result corresponding to the present frame to the image memory.

4. The acoustic wave diagnostic apparatus according to claim 2,
wherein the processor is further configured to notify that the acoustic wave image of the present frame and the measurement result are saved to the user.

5. The acoustic wave diagnostic apparatus according to claim 3,
wherein the processor is further configured to notify that the acoustic wave image of the present frame and the measurement result are saved to the user.

6. The acoustic wave diagnostic apparatus according to claim 2,
wherein the measurement result includes a measurement value, and
the processor is further configured to
compare measurement values measured in past frames among the plurality of continuous frames with the measurement value in the present frame, and
determine that the acoustic wave image of the present frame having the maximum measurement value among the measurement values of the plurality of continuous frames includes the optimum cross section of the measurement target.

7. The acoustic wave diagnostic apparatus according to claim 3,
wherein the measurement result includes a measurement value, and
the processor is further configured to
compare measurement values measured in past frames among the plurality of continuous frames with the measurement value in the present frame, and
determine that the acoustic wave image of the present frame having the maximum measurement value among the measurement values of the plurality of continuous frames includes the optimum cross section of the measurement target.

8. The acoustic wave diagnostic apparatus according to claim 2,
wherein the processor is further configured to
calculate likelihood representing measurement target likeness of the measurement target to be recognized,
compare likelihoods calculated in past frames among the plurality of continuous frames with the likelihood calculated in the present frame, and
determine that the acoustic wave image of the present frame having the maximum likelihood among the likelihoods of the plurality of continuous frames includes the optimum cross section of the measurement target.

9. The acoustic wave diagnostic apparatus according to claim 3,
wherein the processor is further configured to
calculate likelihood representing measurement target likeness of the measurement target to be recognized,
compare likelihoods calculated in past frames among the plurality of continuous frames with the likelihood calculated in the present frame, and determine that the acoustic wave image of the present frame having the maximum likelihood among the likelihoods of the plurality of continuous frames includes the optimum cross section of the measurement target.

10. The acoustic wave diagnostic apparatus according to claim 2,
wherein the processor is further configured to save all acoustic wave images which are captured in a constant time range from the present to the past among the plurality of continuous frames during imaging and the measurement results in the image memory.

11. The acoustic wave diagnostic apparatus according to claim 10,
wherein the processor is further configured to save the acoustic wave image of a frame determined to include the optimum cross section of the measurement target among the plurality of continuous frames during imaging while providing a flag and selects and displays the acoustic wave image provided with the flag among the plurality of acoustic wave images saved in the image memory on the display monitor based on a user's operation through the operating device.

12. The acoustic wave diagnostic apparatus according to claim 1,
wherein upon recognition of a plurality of the measurement targets in the acoustic wave image of the present frame, the processor is further configured to
set the measurement algorithm for each of the plurality of measurement targets in the acoustic wave image of the present frame, and
measure the plurality of measurement targets based on the measurement algorithms corresponding to the plurality of measurement targets in the acoustic wave image of the present frame and displays a plurality of the measurement results on the display monitor to be superimposed on the acoustic wave image of the present frame.

13. The acoustic wave diagnostic apparatus according to claim 1, further comprising:
a measurement control switch that is operated by the user to perform a command to start and a command to end a series of measurement operation including a recognition of the measurement target, the setting of the measurement algorithm, and the measurement of the measurement target, by the processor.

14. The acoustic wave diagnostic apparatus according to claim 13, further comprising:
an acoustic wave probe configured to transmit and receive acoustic waves to and from a subject,
wherein the measurement control switch is disposed in the acoustic wave probe.

15. A method of controlling an acoustic wave diagnostic apparatus that sequentially displays acoustic wave images of a plurality of continuous frames during imaging on a display monitor, the method comprising:
storing measurement algorithms corresponding to a plurality of predetermined organs;
automatically discriminating a type of a measurement target included in an acoustic wave image of a present frame displayed on the display monitor, as one organ among the plurality of predetermined organs, by using a machine learning;
automatically selecting and setting a measurement algorithm corresponding to the one organ among the measurement algorithms;
measuring the measurement target based on the measurement algorithm corresponding to the one organ; and displaying a measurement result on the display monitor to be superimposed on the acoustic wave image of the present frame;

determining whether or not the acoustic wave image of the present frame among the plurality of continuous frames during imaging includes an optimum cross section of the measurement target; and saving acoustic wave image of the present frame which is determined to include the optimum cross section and the measurement result corresponding to the present frame to an image memory by overwriting the acoustic wave image and the measurement result which have been already saved.

\* \* \* \* \*